United States Patent [19]

Mathew et al.

[11] Patent Number: 4,707,294

[45] Date of Patent: Nov. 17, 1987

[54] PREPARATION OF ALCOHOLIC HYDROXYLAMINE SOLUTION FROM HYDROXYLAMMONIUM SULFATE

[75] Inventors: Chempolil T. Mathew, Randolph; Harry E. Ulmer, Morristown, both of N.J.

[73] Assignee: Allied Corporation, Morris Township, N.J.

[21] Appl. No.: 773,711

[22] Filed: Sep. 9, 1985

Related U.S. Application Data

[62] Division of Ser. No. 437,920, Nov. 1, 1982, Pat. No. 4,551,323.

[51] Int. Cl.$^4$ ............................................. C01B 21/14
[52] U.S. Cl. .................................... 252/182; 423/387; 423/545; 423/551; 564/259
[58] Field of Search ....................... 564/259; 252/182; 423/387, 545, 551

[56] References Cited

U.S. PATENT DOCUMENTS 4,551,323 11/1985 Mathew et al. ..................... 423/387

FOREIGN PATENT DOCUMENTS 168305 2/1965 U.S.S.R. ............................. 564/259

Primary Examiner—John Doll
Assistant Examiner—Wayne A. Langel
Attorney, Agent, or Firm—Richard C. Stewart; Gerhard H. Fuchs

[57] ABSTRACT

Solid hydroxylammonium sulfate is reacted with an alcohol solution of an alkali metal hydroxide or alkoxide to produce an alcoholic hydroxylamine liquid phase and a sulfate-containing solid phase. The liquid phase may be used for further reactions such as oxidations, hydroxamic acid production or neutralization to other hydroxylammonium salts. The different bases behave differently with regard to suitable and preferable solvents and temperatures.

4 Claims, No Drawings

PREPARATION OF ALCOHOLIC HYDROXYLAMINE SOLUTION FROM HYDROXYLAMMONIUM SULFATE

This application is a division of application Ser. No. 437,920 filed 11.1.82 now U.S. Pat. No. 4,551,323.

BACKGROUND OF THE INVENTION

Hydroxylamine, usually in the form of salts such as hydroxylammonium sulfate, hydroxylammonium chloride or the like is widely used as a reagent for preparing various industrial, specialty and pharmaceutical chemicals. Reaction of a hydroxylamine reagent with ketones or aldehydes produces oximes. Other reactions of hydroxylamine reagents produce substituted hydroxylamines and hydroxamic acids. Where the organic starting material is either water-soluble or susceptible to an interfacial reaction with an aqueous solution of a hydroxylamine salt, either the chloride or sulfate salt may be used, and the sulfate salt is preferred because of its lower cost. Many products containing oxime or substituted hydroxylamine groups are not susceptible to production in aqueous media. Accordingly, such materials are normally prepared by reaction of solutions of hydroxylammonium chloride in organic solvents such as methanol with the organic precursor in the presence of sufficient base to neutralize the by-product HCl. Because hydroxylammonium sulfate (also called hydroxylamine sulfate) is not soluble in methanol, however, the cheaper sulfate reagent cannot be used to prepare these materials.

BRIEF DESCRIPTION OF THE INVENTION

A process has been discovered which enables solid hydroxylammonium sulfate to be used to provide hydroxylamine values in alcoholic solutions. Accordingly, the present invention includes a process comprising the steps:

(a) reacting an alcoholic solution of a base selected from the group consisting of sodium hydroxide, potassium hydroxide, lithium hydroxide, ammonium hydroxide and the corresponding alkoxides of 1-5 carbons with solid hydroxylammonium sulfate, employing an alcohol of 1-3 carbons, a temperature, a pressure and a time sufficient to produce a liquid phase having at least 50% of the hydroxylamine values of the hydroxylammonium sulfate, and (b) separating the solid phase comprising a sulfate salt corresponding to said base from the liquid phase.

In the simplest form, this process produces an alcoholic solution of free hydroxylamine with little or no water content (depending upon the base used) and a by-product solid phase containing sulfate salts. Depending, however, upon how much base is used, the alcoholic solution produced may be more or less basic than free hydroxylamine. Furthermore, the alcoholic solution may be converted to various salts, including hydroxylammonium chloride and hydroxylammonium nitrate, preferably after separation of the solid phase, and may also be reacted with an organic substrate to produce an oxime or substitued hydroxlyamine or hydroxamic acid product before or after separating the solid phase.

DETAILED DESCRIPTION OF THE INVENTION

Three basic materials used in the process of the present invention are a base, an alcohol solvent and hydroxylammonium sulfate. The hydroxylammonium sulfate is normally in solid form, preferably divided up into relatively fine powder or crystals, and may be produced in a variety of processes including, expecially, that described in U.S. Pat. No. 4,349,520 of Bonfield et al. (Sept. 14, 1982). The alcohol may be any alkanol of 1-3 carbons, expecially methanol or ethanol, but also isopropanol and propanol when the base is an alkoxide. The base may be sodium hydroxide, potassium hydroxide, lithium hydroxide, ammonium hydroxide or an alkoxide. Suitable alkoxides are those of 1-4 carbons such as methoxides, ethoxides, isopropoxides, propoxides and butoxides of sodium, potassium or lithium. It is contemplated, however, that for any particular base, not all alcohols are suitable. Furthermore, for any particular base, specified conditions of temperature and/or pressure may be necessary to achieve the desired conversion of at least about 50% of the hydroxylamine values from the solid hydroxylammonium sulfate to the liquid phase.

In the case of sodium hydroxide as base, any of the alcohols indicated above may be used as solvent. The preferred solvent for use with sodium hydroxide is methanol, with ethanol being slightly less preferred. It has been found that for both methanol and ethanol as solvent, the process of the present invention proceeds to higher conversions at lower temperatures. Thus the reaction temperature, while it may be as high as about 30° C., is preferably no greater than about 20° C. and more preferably no greater than about 10° C. Comparative Example 3, below, illustrates the significantly lower yields obtained at 35°–40° C. compared to those obtained at 22°–25° C. (e.g., Example 2) and at 5°–10° C. (e.g., Example 1). The concentration of sodium hydroxide in methanol or ethanol is not critical, but it is preferred to operate as near to the solubility limit of sodium hydroxide in the alcoholic solvent as possible without creating so viscous a solution that agitation becomes difficult. Larger amounts of the solvent may also be used if tolerable in subsequent reactions. Various of the examples illustrate the use of relatively concentrated methanolic and ethanolic solutions of sodium hydroxide in the present process. The amount of sodium hydroxide should be at least that required to neutralize 50% of the hydroxylammonium sulfate reacted, preferably at least that necessary to neutralize all of the hydroxylammonium sulfate. It is contemplated that greater amounts of sodium hydroxide than that stoichiometrically required may be used and, as indicated in Example 9 below, such excess sodium hydroxide may increase the reaction rate without detracting from reaction yields. Excess sodium hydroxide is normally to be used, however, only if the product alcoholic solution is to be used as a reagent in processes where more base would normally be charged at a later time. In other cases, the excess base can be neutralized before the solution is used further. Thus, the product solution can be formed at any desired pH such as from 5 to 12.

In using sodium hydroxide in ethanol as the solvent, lower temperatures are still preferred, with reaction below about 30° C., preferably below about 20° C. and more preferably no greater than about 10° C. being contemplated. It appears, however, that the reaction in ethanol is less temperature dependent than the reaction in methanol (see Examples 11 and 12 below).

Potassium hydroxide behaves quite differently from sodium hydroxide in the process of the present invention. First, methanol is not a suitable solvent for use with potassium hydroxide. As indicated in Comparative Examples 15 and 16 below, reaction of potassium hydroxide in methanol with hydroxylammonium sulfate produces extremely low yields either at 10° C. or at 22°–25° C. As indicated in Examples 17 and 18 below, however, potassium hydroxide in ethanol is a highly effective means of conducting the present process. These examples demonstrate that the reaction of potassium hydroxide in ethanol with hydroxylammonium sulfate proceeds at a slightly greater rate and to a slightly greater conversion at 22°–25° C. than at 5°–10° C. Accordingly, any temperature not greater than about 40° C. may be used with potassium hydroxide as the base, with temperatures of about 15° to about 25° C. being preferred. Temperatures above 40° C. should not normally be employed, however, since the product free hydroxylamine is likely to decompose significantly faster at such temperatures. As in the case of sodium hydroxide, potassium hydroxide may be used at any concentration and in any amount relative to the hydroxylammonium sulfate charged. Again, however, it is preferred in many cases to use a saturated or nearly saturated solution of potassium hydroxide in ethanol rather than dilute solution. It is also preferred to use, relative to the stoichiometric amount of potassium hydroxide, at least that needed to neutralize 50% of the hydroxylammonium sulfate, preferably at least that necessary to neutralize all of the hydroxylammonium sulfate. Excesses of potassium hydroxide may also be used.

Lithium hydroxide, as a base in the present invention, may be used with methanol or ethanol. The reaction appears to proceed to slightly higher conversions at higher temperatures, as indicated by Examples 13 and 14 below. Neverless, any temperature up to about 40° C. may be used, with a range of about 10° to about 40° C. being preferred, and a range of about 15° to about 25° C. being more preferred. The reaction of lithium hydroxide in methanol appears to proceed at a slower rate and/or to a lower final conversion than either the reaction of sodium hydroxide in methanol or ethanol or the reaction of potassium hydroxide in ethanol. The above comments relating to concentration of base in the alcohol and to amounts of base relative to hydroxylammonium sulfate made in respect to sodium hydroxide and potassium hydroxide apply equally to lithium hydroxide.

While isopropanol or propanol may be used as solvents with NaOH, KOH, or LiOH, the limited solubilities of these hydroxides and of the product hydroxylamine in these solvents makes these embodiments less preferred to those described above.

Ammonium hydroxide, as a base, may be used with any of the lower alcohols in a manner similar to that employed with lithium hydroxide. The term "ammonium hydroxide" is intended to include ammonia plus some amount of water, such as equimolar amounts of ammonia and water, or half or twice the equimolar amount of water. Using ammonia without any water is not considered satisfactory, based on the poor yields shown in comparative Examples 20–24, below.

In using sodium hydroxide, potassium hydroxide or lithium hydroxide, pressure is not a critical factor since neither the base nor the solvent is very volatile. Only when methanol or ammonia is used, is pressure at all a factor, and even then atmospheric or even pressures below atmospheric may be used, but pressures at or above atmospheric pressure are preferred, and atmospheric pressure is more preferred.

Alkoxides such as sodium methoxide, ethoxide, isopropoxide, propoxide, butoxide and pentylate may be used in place of the hydroxides, having the advantage of not producing water as by-product. Therefore, when a substantially water-free hydroxylamine solution is desired, these more expensive alkoxide bases should be used. Normally, the solvent will correspond to the anion (e.g., sodium methoxide in methanol), but mixed systems (e.g., sodium butoxide in methanol) may be used if the solvent later present (after the hydroxylamine-consuming reaction) is not to be recovered and recycled or can be distilled. While the anion may be larger than three carbons, the solvent is normally a 1–3 carbon alkanol (and is preferably methanol or ethanol) because free hydroxylamine is more soluble in these lower alkanols.

In similar fashion, the alkoxides of lithium and potassium may be used, except that potassium alkoxides would normally not be used with methanol as solvent.

Alkoxides are more expensive than hydroxides and are, therefore, normally not used unless the 3% or so water in the product solution of the above reactions of hydroxides cannot be tolerated for a particular use. The present invention, using alkoxides still makes available the use of cheaper hydroxylammonium sulfate for such water-sensitive uses.

In each ease, one preferred mode of conducting the reaction is to first dissolve (or slurry) the base in the alcohol and then react the alcoholic solution with hydroxylammonium sulfate. As illustrated by Examples 1 and 8, below, essentially identical results can be achieved either by adding the solid hydroxylammonium sulfate to the alcoholic solution or by adding the alcoholic base to the solid hydroxylammonium sulfate. Furthermore, it is contemplated that the two may be mixed in any conventional batch or continuous process scheme normally used to react a solid with a liquid. A less preferred method of conducting the present invention is to mix the base (solid or gas) with the hydroxylammonium sulfate first, and then to add the alcohol. This scheme is less preferred because the process of dissolving the base in the alcohol (which is required before the reaction can occur) is normally an exothermic reaction. Since high temperatures are generally not required (and in the case of sodium hydroxide are preferably avoided), it is desirable that the act of dissolving base in alcohol be conducted first, that the alcoholic solution be cooled and that the cooled alcoholic solution be reacted with the hydroxylammonium sulfate. Another less preferred method is to add the base slowly to hydroxylammonium sulfate slurried in alcohol.

Once the reaction between alcoholic base and hydroxylammonium sulfate is complete, or while it is proceeding, the alcoholic solution containing hydroxylamine values may be further reacted with either a mineral acid or an organic reagent such as as aldehyde or ketone. In one mode, this reaction is conducted after separating the by-product sulfate (e.g., sodium sulfate) from the alcoholic hydroxylamine solution. Thus, as illustrated in the Examples below, the alcoholic hydroxylamine solution is reacted with methyl ethyl ketone to produce methyl ethyl ketone oxime. Such reaction may be conducted in the pH normally used for the reaction involved, with pH between about 5 and about 8 used to convert ketones of aldehydes to oximes. The separated hydroxylamine-containing liquid phase may also be reacted with acids such as HCl, nitric acid, phosphoric acid, perchloric acid or oxalic acid to produce the corresponding hydroxylammonium salt (e.g., hydroxylammonium chloride or hydroxylammonium nitrate). Excess base may be removed by neutralizing to pH 7–9 before separating the sulfate solids and introducing the other acids (as in Examples 25-28). If it is desired to recover such salt in solid form, the alcohol may be evaporated off (preferably under vacuum) or may be precipitated by the addition of a non-solvent for the salt such as a hydrocarbon. It is contemplated that such further reaction of hydroxylamine, may be conducted prior to separating the by-product sulfate, such as by having a ketone present in or added with the alcoholic sodium hydroxide solution. In such case, as free hydroxylamine becomes available in the alcoholic solution, it reacts with ketone or aldehyde (provided that the proper pH is reached). Reaction of alcoholic hydroxylamine with a mineral acid is preferably, however, conducted only after the by-product sulfate salt is removed.

The step of removing the by-product solid sulfate from alcoholic solution containing hydroxylamine values may be carried out using any conventional technique for separating a solid from a liquid. Centrifugation, filtration, decantation and other conventional engineering steps are included. It is preferred that the recovered solid be washed with a solvent (such as the alcohol used for the solution) to remove adhered hydroxylamine-containing alcohol. Thereafter the solid may be dried, washed or recrystallized, treated in other ways to recover unreacted hydroxylammonium sulfate, or disposed of as initially separated.

The present invention is illustrate by the follwing Examples, which are not intended to limit the invention:

EXAMPLE 1

A solution of methanolic sodium hydroxide was prepared by mixing sodium hydroxide pellets (17.2 g; 0.43 mol) with absolute methanol (150 mL) in a 250 mL Erlenmeyer flask.

In the meantime a 500 mL 3-necked flask was fitted with a thermometer, dropping funnel and nitrogen inlet (inert atmosphere) and a magnetic stirring bar (PTFE-coated, 1½ inches or 3.8 cm long) was placed in it. Solid hydroxylamine sulfate (35 g; 0.213 mol) was placed in the flask with methanol (50 mL) and the flask was placed in an ice-water bath over a stir plate. With vigorous stirring, the methanolic NaOH solution was added slowly (over 5 minutes) using the dropping funnel, maintaining the reaction mixture temperature below 10° C. After the addition was complete, stirring was continued for 1½ hours more with cooling (5°–10° C.). A white slurry resulted and this was filtered over a Buchner funnel and the cake was washed with more methanol (25 mL). The clear and colorless filtrate (pH 12.5) was analyzed for free hydroxylamine by mixing with known excess of methyl ethyl ketone (MEK) (40 g) and adjusting the pH to 7 with concentrated $H_2SO_4$ (2.5 g). Methyl ethyl ketoxime formed was determined by gas chromatography to correspond to free hydroxylamine (87.4% yield).

The white filter cake (34.2 g) of sodium sulfate was analyzed for remaining hydroxylamine sulfate by dissolving in water (150 mL) and mixing with excess of MEK (40 g) and titrating with 50% NaOH solution (3.9 g) to pH 7. The amount of hydroxylamine sulfate left in the cake represented 11.4% of the total.

EXAMPLE 2

A 500 mL resin flask was fitted with thermometer, dropping funnel, nitrogen inlet and a stainless steel propeller-type over-head stirrer. Hydroxylamine sulfate crystals (35 g; 0.213 mol) were mixed with methanol (50 mL); and, with vigorous stirring but no extraneous cooling, a methanolic solution of NaOH (17.2 g; 0.43 mol) in methanol (150 mL) was added over 5 minutes. Agitation was continued for 2 hours at ambient temperature (22°–25° C.).

The white slurry was worked up as in Example 1. The filtrate (with methanol wash) was analyzed as in Example 1 by gas chromatography. (Yield 71.2%).

COMPARATIVE EXAMPLE 3

As in Example 1, the experiment was conducted in a 500 mL 3-necked flask using a PTFE-coated magnetic stirrer. Hydroxylamine sulfate (35 g; 0.213 mol) as a slurry in methanol (50 mL) was treated with vigorous stirring with sodium hydroxide solution prepared from NaOH pellers (17.2 g; 0.43 mol) and methanol (150 mL). During the addition and subsequent stirring (1½ hours) the temperature was maintained at 35°–40° C. using a circulating bath.

The filtrate with methanol wash (214.6 g) was mixed with MEK (40 g) and adjusted pH to 7 with concentrated $H_2SO_4$ (16.9 g). Gas chromatographic analysis of MEK oxime produced showed the yield to be 18.8%. The filter cake (35.4 g) required 26.5 g of 50% NaOH solution to neutralize, suggesting that 76.5% of hydroxylamine sulfate was left unused.

This example shows that poorer yields are obtained at 35°–40° C.

EXAMPLE 4

The experiment was conducted exactly as in Example 1, using a magnetic stirrer in a 500 mL 3-necked flask. Hydroxylamine sulfate (35 g; 0.213 mol) was reacted with NaOH (17.2 g; 0.43 mol) using total methanol (163 mL). Temperature was maintained at 5°–10° C. as the mixture was stirred for 6 hours.

The filtrate (pH 8.4 ) was analyzed in the usual manner and was found to account for 90.7% yield of hydroxylamine. The solid cake (36 g) required 0.3 g of 50% NaOH, which suggested that a trace amount (0.9%) of hydroxylamine sulfate was present in the solid cake.

EXAMPLE 5

The experiment was conducted exactly as in Example 4. The reaction mixture was maintained at about 10° C. for the first 6 hours and then stirred at ambient temperature (about 22° C.) for 12 hours more. At the end of 18 hours the slurry was worked up as usual.

The filtrate (pH 6.5 ) accounted for 80.5% yield of hydroxylamine, while the filter cake showed virtually no hydroxylamine sulfate left.

EXAMPLE 6

The same equipment as in Example 1 was used. A total of 200 mL of methanol was used to slurry hydroxylamine sulfate (35 g; 0.213 mol) with NaOH (17.2 g; 0.43 mol). The reaction was conducted below 10° C. using ice water bath for 4 hours with vigorous stirring.

The filtrate, when analyzed in the usual manner (gas chromatography), showed 91.6% yield of free hydroxylamine. The cake required 2.6 g of 50% NaOH representing 7.6% of hydroxylamine sulfate.

EXAMPLE 7

Sodium hydroxide pellets (103.2 g; 2.58 mol) were dissolved in absolute methanol (750 mL) and added slowly (15 minutes) to a stirred slurry of hydroxylamine sulfate (210 g; 1.28 mol) with methanol (228 mL) placed in a 2 liter, 3-necked flask fitted with thermometer, dropping funnel and an overhead glass stirrer with three inch long PTFE paddle. A five-eighths inch wide PTFE baffle was also introduced into the liquid to provide good agitation. The temperature during the addition and subsequent stirring (4 hours) was maintained at 5° C. using a thermostated bath.

The white slurry at the end of stirring was filtered and the cake washed with more methanol. The total filtrate (845.5 g) was analyzed by gas chromatography after conversion to MEK oxime by mixing with MEK and adjusting pH to 7 (from pH 12.9) using concentrated $H_2SO_4$ (21.0 g). Yield 82.1% hydroxylamine.

The wet cake (208.5 g) was dissolved in water (900 g) and mixed with MEK (200 g) and then neutralized with 50% NaOH solution (35.8 g). The leftover hydroxylamine sulfate in the cake corresponded to 17.3% of the total sulfate used.

EXAMPLE 8

The experiment was conducted using the same equipment as in Example 1. Sodium hydroxide (17.2 g; 0.43 mol) was dissolved in methanol (200 mL) and the solution was placed in the 500 mL flask. With stirring and cooling (5°–10° C.) solid hydroxylamine sulfate was added using a spatula over 20 minutes. The mixture was then stirred for 1.5 hours more and the white slurry filtered.

The filtrate on analysis in the usual manner showed 86.6% of the hydroxylamine. The solid on analysis was found to contain 10.4% of hydroxylamine sulfate that was started with.

EXAMPLE 9

A solution of NaOH pellets (34.4 g; 0.86 mol) in methanol (250 mL) was added to hydroxylamine sulfate (35 g; 0.213 mol) mixed with methanol (38 mL) with vigorous agitation in a 500 mL 3-necked flask. Temperature was maintained at 7°–10° C. during the stirring of one hour.

The slurry was filtered and analyzed as usual. The filtrate showed 78.3% yield of free hydroxylamine. The filter cake was found to contain 12.2% of hydroxylamine sulfate.

EXAMPLE 10

The equipment as in Example 1 was used. NaOH (17.2 g; 0.43 mol) was discovered in methanol (150 mol) and mixed with water (7.5 mL); and this solution was added to hydroxylamine sulfate (35 g; 0.213 mol) suspended in methanol (50 mL). Temperature was maintained between 5° and 10° C. during the addition, and vigorous stirring for 2 hours with cooling.

The white slurry was filtered and the cake washed on the filter with more methanol (25 mL). The total filtrate on analysis (gas chromatography) showed 70.8% yield of free hydroxylamine. Analysis of the crude cake (37.0 g) showed that it contained 27.9% of hydroxylamine sulfate.

This example shows that added water had no beneficial effect.

EXAMPLE 11

Sodium hydroxide pellets (17.2 g; 0.43 mol) were stirred over nearly two hours in a 500 mL Erlenmeyer flask with absolute ethanol (200 mL) till a clear solution was obtained. The solution was placed in a 250 mL dropping funnel which in turn was placed on a 500 mL 3-necked flask fitted with thermometer and a drying tube (Drierite TM). A 1.5 inch long PTFE-coated stirring rod was placed in the flask along with hydroxylamine sulfate (35 g; 0.213 mol) and absolute ethanol (20 mL). As the contents were stirred vigorously over the stir-plate with cooling in an ice water bath (5°–10° C.), the ethanolic solution of NaOH was added slowly (10 minutes). The slurry was continued to be stirred vigorously for 3 hours with cooling. The white slurry produced was filtered and the filter cake washed with more ethanol (25 mL).

The white solid cake (38.6 g) was analyzed in the usual manner and was found to contain hydroxylamine sulfate representing 4.7% of the starting amount. The clear filtrate was analyzed by gas chromatography after mixing with excess MEK (40 g) and adjusting the pH to 7 with concentrated $H_2SO_4$. Yield 88.3%.

EXAMPLE 12

The experiment was performed exactly as in Example 11, except that the temperature during the mixing of reactants and subsequent stirring was maintained between 22° and 25° C. At the end of 3 hours of stirring, the filtrate with washing was analyzed as usual and showed 89.1% yield of free hydroxylamine.

The white solid (36.0 g) on neutralization with 50% NaOH (1.0 g) showed the presence of 2.9% hydroxylamine sulfate left in the cake.

EXAMPLE 13

The equipment as in Example 1 was used and a solution of lithium hydroxide monohydrate (LiOH.$H_2O$; 18.0 g; 0.428 mol) in methanol (200 mL) was added with stirring to a mixture of hydroxylamine sulfate (35 g; 0.213 mol) and methanol (20 mL). Temperature was maintained at 10° C. during the stirring for 1.5 hours. The white slurry on filtration furnished a clear filtrate and a white solid cake.

The filtrate on analysis (gas chromatography) showed 45.8% free hydroxylamine in solution. The wet solid cake (41 g) was found to contain hydroxylamine sulfate corresponding to 42.6% of the orginal amount.

EXAMPLE 14

The experiment was repeated exactly as in Example 13, except that embient temperature (22°–24° C.) was maintained throughout. Stirring was continued for 3 hours and the slurry was filtered.

The solid (38.0 g) was found to contain 13.1% of the total hydroxylamine sulfate. The filtrate on analysis showed 53.8% yield of free hydroxylamine.

COMPARATIVE EXAMPLE 15

The equipment as in Example 1 was used. Potassium hydroxide pellets (24.0 g; 0.428 mol) were dissolved in methanol (150 mL) and the clear solution was added slowly (5 minutes) to a stirred slurry of hydroxylamine sulfate (35.0 g; 0.213 mol) in methanol (50 mL). With the temperature maintained at 10° C., stirring was continued for 3 hours.

On filtering a clear filtrate was collected along with a crystalline solid cake. Analysis of the filtrate by gas chromatography after conversion to MEK oxime showed that virtually no hydroxylamine (<1.0%) was liberated. The crystalline solid was found to be virtually pure hydroxylamine sulfate.

COMPARATIVE EXAMPLE 16

The experiment was conducted exactly as in Comparative Example 15, using KOH (24.0 g; 0.428 mol), methanol (200 mL total) and hydroxylamine sulfate (35.0 g; 0.213 mol). Ambient temperature (22°-25° C.) was maintained during the addition and susequent stirring (1 hour).

On filtration a crystalline solid was collected, and this was found to be virtually pure hydroxylamine sulfate. The filtrate on analysis showed less than 5% yield of hydroxylamine.

EXAMPLE 17

The 500 mL 3-neck flask as in Example 1 was used. Potassium hydroxide pellets (24.0 g; 0.428 mol) were dissolved in ethanol (150 mL) and added to a slurry of hydroxylamine sulfate (35.0 g; 0.213 mol) with ethanol (50 mL) over 5 minutes with no extraneous cooling. The temperature during the addition and subsequent stirring over 3 hours remained between 22° and 25° C.

A white slurry resulted and this filtered and the white solid on the filter washed with more ethanol. The clear filtrate with washings was analyzed to contain 77.9% yield of free hydroxylamine. The wet cake (43.0 g) was dissolved in water and analyzed for unreacted hydroxylamine sulfate (16.6%).

EXAMPLE 18

. The experiment was performed exactly as in Example 17, except that the temperature was maintained throughout the mixing and subsequent stirring period (3 hours) at 5°-10° C. using an ice-water bath.

The filtrate (204 g) on analysis (gas chromatography) gave a yield of 70.0% of free hydroxylamine. The solid (38.0 g) was found to contain (24.1%) of the hydroxylamine sulfate that was orginally used.

EXAMPLE 19

In a 500 mL resin flask fitted with an overhead stirrer was placed hydroxylamine sulfate (35.0 g; 0.213 mol) mixed with methanol (200 mL) and water (10 mL). To the slurry (pH 4.2) was bubbled ammonia gas from a cylinder till the pH rose to 9.0 with stirring and cooling in water bath. At the end of one hour stirring pH had dropped to 6.6. More ammonia was introduced (pH 9.0) and stirring continued. This was repeated several times over a total of 3 hours. Finally, when the pH did not change after bringing up to 9.5 and stirring over 15 minutes, the slurry was filtered and the clear filtrate analyzed. The hydroxylamine content in the filtrate was determined to be 46.7% of theoretical yield.

The white filter cake after dissolving in water was analyzed and found to contain 42.4% of the orginial hydroxylamine sulfate started with.

COMPARATIVE EXAMPLE 20

Ammonia gas was dissolved in absolute methanol and a solution containing 11.6% $NH_3$ was prepared. Portion of this solution (88 g=10.2 g $NH_3$) was added to a slurry of hydroxylamine sulfate (35 g; 0.213 mol) in methanol (100 mL) in a 500 mL 3-neck flask provided with magnetic stirring bar. The flask was cooled in ice water bath (5°-10° C.) and the slurry was stirred vigorously for 3 hours. It was filtered and the cake washed with methanol to furnish a solution (176 g). This clear solution was analyzed potentiometrically and found to contain 17.1% yield of hydroxylamine.

The white solid (33 g) was dissolved in water and analyzed and found to contain 78.5% hydroxylamine sulfate still present unused.

COMPARATIVE EXAMPLE 21

Ammonia solution in methanol (100 g=11.7 g $NH_3$) was added to hydroxylamine sulfate (35 g; 0.213 mol) and methanol (100 mL) in a 500 mL autoclave and the reactor quickly sealed. The contents were stirred for 3 hours with cooling at 10° C. No pressure development was noticed throughout.

The slurry was filtered and the cake washed with methanol. The total filtrate (263 g) on analysis potentiometrically showed the presence of free hyroxylamine corresponding to 10.0% of theoretical. The crude solid (32.5 g) contained 82.8% of unused hydroxylamine sulfate.

COMPARATIVE EXAMPLE 22

In a 500 mL autoclave was placed solid hydroxylamine sulfate (35 g; 0.213 mol) mixed with methanol (50 mL) and a solution of ammonia in methanol (150 g of 7.4% solution=11.1 g $NH_3$) was added quickly and the autoclave sealed. The contents were heated (40°-50° C.) and stirred very vigorously for 2 hours. Slight pressure development was noticed during the heating, but the pressure disappeared as it was cooled to ambient temperature.

The contents were filtered and a colorless filtrate (196 g) collected along with white solid (32 g). The filtrate was analyzed potentiometrically and found to contain 5.7% yield of hydroxylamine. The solid contained 84.0% of unreacted hydroxylamine sulfate.

COMPARATIVE EXAMPLE 23

The same 500 mL autoclave as in previous example was used. A solution of $NH_3$ in ethanol (150 g, 5.7%=8.55 g $NH_3$) was added quickly to hydroxylamine sulfate (35 g; 0.213 mol) and ethanol (50 mL) in the autoclave. After sealing the reactor, it was stirred at ambient temperature (19° C.) for 3 hours.

On filtration of the contents and washing with ethanol, a clear, colorless liquid (232 g) was collected which on analysis as usual showed 13.9% yield of free hydroxylamine. The solid (32 g) contained hydroxylamine sulfate corresponding to 76.7% of the amount started with.

COMPARATIVE EXAMPLE 24

In a 500 mL 3-neck flask was placed hydroxylamine sulfate (35 g; 0213 mol) and solution of sodium hydroxide pellets (17.2 g; 0.43 mol) in ethylene glycol (300 g) was added with stirring using a magnetic stirring bar. Stirring was continued over a total of 3 hours, first 2 hours at room temperature and the last hour at 30° C.

After filtering the viscous slurry, the filtrate was analyzed potentiometrically and was found to have hydroxylamine equal to 7.4% yield. The white solid (32 g) was analyzed and found to contain 75.3% of the orginial hydroxylamine sulfate.

EXAMPLE 25

In a 500 mL 3-necked flask was placed hydroxylamine sulfate (70 g; 0.43 mol) with methanol (50 mL). To this was added with stirring using magnetic stirring bar a solution of NaOH pellets (34.4 g; 0.86 mol) in methanol (300 mL) over 15 minutes with cooling in an ice-water bath. Stirring was continued over 3 hours at temperatures ranging from 2° to 7° C. The pH of the slurry was recorded (11.2) and conc. $H_2SO_4$ (1.5 g) was added dropwise untio pH 8.0 was reached.

The white slurry was filtered and the cake washed on the filter with more methanol. The total filtrate (323 g) was analyzed potentiometrically and found to contain free hydroxylamine corresponding to 85.2% of the starting sulfate.

The filtercake (69 g) was analyzed for hydroxylamine sulfate left behind (10.9%).

The methanolic solution of hydroxylamine was placed in a 500 mL Erlenmeyer containing a magnetic stirring bar and the flask in turn was placed in an ice bath over a stir plate. HCl gas was slowly bubbled into the solution with stirring and maintaining the temperature at 20°–25° C. HCl addition was continued until the pH dropped from 8.0 to 2.8. The solution was then placed in a 1 liter round bottom flask and evaporated to dryness under reduced pressure. White crystalline solid of hydroxylamine hydrochloride (49.9 g) was collected (M.P. 154.5° C.) yield 84.1%.

EXAMPLE 26

A solution sodium methoxide in methanol produced by dissolving sodium (10 g; 0.435 mol) in methanol (150 mL) was stirred with hydroxylamine sulfate (35 g; 0.213 mol) in ice-water bath (5°–10° C.) over 2 hours. The slurry filtered and the clear methanolic filtrate with cake-wash (pH 9.2) was mixed with conc. $H_2SO_4$ (0.8 g) to pH 8.0. The thin white solid produced was filtered off and the clear filtrate was placed in 500 mL Erlenmeyer with a magnetic stirring bar. While cooling in ice-water and stirring, conc. $HNO_3$ (35.5 g) was added till the pH reached 2.8. The clear methanolic solution of hydroxylamine nitrate (273.3 mL) was found to contain 37.99 g $NH_2OH.HNO_3$ (13.9 g in 100 mL). Overall yield 92.7%.

EXAMPLE 27

A solution of hydroxylamine in methanol prepared as in Example 7 was used. The solution (100 ml containing 4.84 g $NH_2OH$) was placed in a 250 mL 3-neck flask fitted with thermometer and a dropping funnel and containing a magnetic stirring bar. With stirring and cooling in an ice-water bath (5° C.) 85% othophosphoric acid (8.0 g; 0.069 mol) was slowly added till pH of the solution dropped from 11.8 to 8.0, and a bulky-white slurry was produced. After stirring at 5° C. for 15 minutes more, the solid was collected by filtration (11.8 g crude cake). It was recrystallized from hot water, and white crystalline hydroxylammonium phosphate (8.2 g on drying) was collected. Yield 85.4% (M.P. 175° C. with decomposition).

EXAMPLE 28

A solution of hydroxylamine in methanol (680 mL) as in Example 27 was used (pH 11.8). Conc. $H_2SO_4$ was slowly added to adjust the pH to 8.0 and the thin white precipitat formed was filtered off and the clear filtrate placed in a 1 liter Erlenmeyer flask. A magnetic stirring bar was introduced and the flask was placed in an ice-water bath. Oxalic acid (45 g; 0.5 mol) dissolved in methanol (100 mL) was slowly added with cooling and stirring. A thick white slurry was produced and this was filtered and the crude white solid (84.8 g) was collected. A portion (25 g) of this solid was recrystallized from hot water to produce white crystalline hydroxylammonium oxalate (M.P. 192° C. with decomposition). Yield 94.6%.

EXAMPLE 29

A 500 mL 3-necked flask was fitted with a thermometer, reflux-condenser and drying tube. Freshly cut sodium (10.0 g; 0.435 mol) was placed in the flask and absolute methanol (175 mL) was carefully added with cooling. After the sodium was completely dissolved in methanol forming a clear solution of sodium methoxide, solid hydroxylamine sulfate (35 g; 0.213 mol) was added with cooling over 2 minutes. No significant exotherm was noticed. The mixture was stirred with cooling (10° C.) in ice-water bath using a magnetic stirring bar over a stir plate for one hour. Subsequently, cooling was removed and vigorous stirring continued at ambient temperature for 2 hours more. By this point a white slurry had formed, and this was filtered and the cake washed using more methanol. The total filtrate (162 g) was analyzed potentiometrically and found to contain hydroxylamine corresponding to 87.5% yield. The filtrate was virtually free of water (<0.5% $H_2O$).

The white solid (32 g) was dissolved in water and analyzed for unused hydroxylamine sulfate (1.6%).

COMPARATIVE EXAMPLE 30

In a 500 mL 3 neck flask fitted with thermometer, reflux condenser, and drying tube was placed absolute methanol (100 mL) and freshly-cut potassium (8.4 g; 0.215 mol) was added piece-by-piece with cooling in ice-bath and a clear solution of potassium methoxide in methanol was produced. To this solution was added with vigorous stirring crystalline hydroxylamine sulfate (17.5 g; 0.107 mol) and stirring was continued at ambient temperature for 3 hours. No noticeable change (no milkiness) was found to be developing.

The slurry was filtered and the filter cake was washed with more methanol. The total filtrate (125 g) was analyzed potentiometrically and found to contain virtually no hydroxylamine (<0.3% yield). The crude filter cake (18 g) which appeared crystalline (similar to the starting hydroxylamine sulfate) was dissolved in water (75 mL) and analyzed and found to contain over 95% of the starting hydroxylamine sulfate.

What is claimed is:
1. A process comprising the steps of:
   (a) reacting an alcoholic solution of a base selected from the group consisting of sodium hydroxide, potassium hydroxide, lithium hydroxide, ammonium hydroxide and the corresponding alkoxide of 1–5 carbons with solid hydroxyammonium sulfate, employing an alcohol of 1–3 carbons, a temperature, a pressure and a time sufficient to produce a liquid phase having at least 50% of the hydroxyamine values of the hydroxylammonium sulfate;
   (b) reacting said hydroxylamine values in said liquid phase with an organic reagent; and
   (c) separating the solid phase comprising a sulfate salt corresponding to said base from the liquid phase.

2. A process comprising the steps of:
(a) reacting an alcoholic solution of a base selected from the group consisting of sodium hydroxide, potassium hydroxide, lithium hydroxide, ammonium hydroxide, and the corresponding alkoxides of 1-5 carbons with solid hydroxylammonium sulfate, employing an alcohol of 1-3 carbons, a temperature, a pressure and a time sufficient to produce a liquid phase having at least 50% of the hydroxylamine values of the hydroxylammonium sulfate;

(b) separating the solid phase comprising a sulfate salt corresponding to said base from the liquid phase; and (c) reacting the liquid phase containing hydroxylammonium values with an acid other than sulfuric acid to produce a hydroxylammonium salt other than hydroxylammonium sulfate.

3. The process of claim 2 wherein the other acid is HCl and the product solution is alcoholic hydroxylammonium chloride.

4. The process of claim 3 wherein said other acid is nitric acid and the product solution is an alcoholic solution of hydroxylammonium nitrate.

* * * * *